(12) United States Patent
Opolski

(10) Patent No.: US 7,618,435 B2
(45) Date of Patent: *Nov. 17, 2009

(54) MAGNETIC ATTACHMENT SYSTEMS

(75) Inventor: Steven W. Opolski, Carlisle, MA (US)

(73) Assignee: NMT Medical, Inc., Boston, MA (US)

( * ) Notice: Subject to any disclaimer, the term of this patent is extended or adjusted under 35 U.S.C. 154(b) by 357 days.

This patent is subject to a terminal disclaimer.

(21) Appl. No.: 10/379,058

(22) Filed: Mar. 4, 2003

(65) Prior Publication Data

US 2004/0176797 A1    Sep. 9, 2004

(51) Int. Cl.
*A61B 17/08* (2006.01)
(52) U.S. Cl. .......................................... 606/213; 606/1
(58) Field of Classification Search ................ 606/213, 606/1, 205–211; 7/168, 901; 81/451; 294/65.5; 600/7, 377, 12
See application file for complete search history.

(56) References Cited

U.S. PATENT DOCUMENTS

| | | | | |
|---|---|---|---|---|
| 512,381 | A * | 1/1894 | Keyes ........................ 294/65.5 |
| 2,625,967 | A * | 1/1953 | Stull .......................... 81/57.42 |
| 2,678,578 | A * | 5/1954 | Bonanno ...................... 81/436 |
| 2,970,002 | A * | 1/1961 | Laviano ...................... 294/65.5 |
| 4,134,405 | A * | 1/1979 | Smit .......................... 606/108 |
| 4,784,646 | A | 11/1988 | Feingold |
| 4,790,809 | A | 12/1988 | Kuntz |
| 4,792,320 | A | 12/1988 | Nickel |
| 4,813,729 | A * | 3/1989 | Speckhart .................. 294/65.5 |
| 4,817,600 | A | 4/1989 | Herms et al. |
| 4,865,030 | A | 9/1989 | Polyak |
| 4,940,452 | A | 7/1990 | Rohe et al. |
| 4,969,879 | A | 11/1990 | Lichte |
| 4,994,019 | A | 2/1991 | Fernandez et al. |
| 5,122,123 | A | 6/1992 | Vaillancourt |
| 5,169,193 | A * | 12/1992 | Stelmach .................... 294/65.5 |
| 5,214,019 | A * | 5/1993 | Nalette et al. ............... 502/400 |
| 5,265,887 | A * | 11/1993 | Stelmach .................... 294/65.5 |
| 5,282,826 | A | 2/1994 | Quadri |
| 5,380,338 | A | 1/1995 | Christian |
| 5,411,519 | A | 5/1995 | Tovey et al. |
| 5,425,744 | A | 6/1995 | Fagan et al. |
| 5,429,131 | A * | 7/1995 | Scheinman et al. ......... 600/374 |
| 5,509,888 | A | 4/1996 | Miller |
| 5,511,559 | A | 4/1996 | Vance |
| 5,638,727 | A * | 6/1997 | Gringer ....................... 81/438 |
| 5,653,730 | A * | 8/1997 | Hammerslag ............... 606/214 |
| 5,702,421 | A | 12/1997 | Schneidt |
| 5,725,552 | A | 3/1998 | Kotula et al. |

(Continued)

FOREIGN PATENT DOCUMENTS

AU    614987    12/1988

(Continued)

OTHER PUBLICATIONS

Latson, (1993), "Transcatheter Closure of Atrial Septal Defects," *Transcatheter Therapy in Pediatric Cardiology*, pp. 335-348.

*Primary Examiner*—Darwin P Erezo

(57) ABSTRACT

A magnetic attachment device is provided for use in a transcatheter delivery system. The system may be useful for delivering, repositioning, and removal of an implant, such as a septal occluder, in or out of a patient.

16 Claims, 8 Drawing Sheets

U.S. PATENT DOCUMENTS

| | | |
|---|---|---|
| 5,752,973 A | 5/1998 | Kieturakis |
| 5,782,149 A * | 7/1998 | Jensen .................. 81/125 |
| 5,984,378 A | 11/1999 | Ostrander et al. |
| 6,007,558 A | 12/1999 | Ravenscroft et al. |
| 6,171,329 B1 | 1/2001 | Shaw et al. |
| 6,206,835 B1 | 3/2001 | Spillman, Jr. et al. |
| 6,231,516 B1 | 5/2001 | Keilman et al. |
| 6,258,098 B1 | 7/2001 | Taylor et al. |
| 6,264,601 B1 | 7/2001 | Jassawalla et al. |
| 6,319,191 B1 | 11/2001 | Sayet et al. |
| 6,417,750 B1 | 7/2002 | Sohn |
| 6,551,304 B1 * | 4/2003 | Whalen et al. ................. 606/1 |
| 6,652,569 B1 * | 11/2003 | Taylor et al. ............... 623/1.11 |
| 7,226,466 B2 * | 6/2007 | Opolski ...................... 606/213 |
| 2002/0022793 A1 | 2/2002 | Bertrand et al. |
| 2002/0040178 A1 | 4/2002 | Sayet et al. |
| 2002/0049366 A1 | 4/2002 | Kehr |
| 2003/0181945 A1 | 9/2003 | Opolski et al. |

FOREIGN PATENT DOCUMENTS

| | | |
|---|---|---|
| DE | 27 21 752 | 11/1978 |
| DE | 36 10 825 A1 | 10/1987 |

* cited by examiner

MAGNETIC ATTACHMENT SYSTEMS

TECHNICAL FIELD

The invention generally involves attachment devices used in transcatheter delivery systems and their uses in connection with delivering or relocating a medical implant, more specifically, an intracardiac prosthetic occluder.

BACKGROUND OF THE INVENTION

Numerous systems have been devised over the years in order to assist medical personnel in delivering and positioning medical implants, for example, prosthetic occluders, within the human body, preferably, in a minimally invasive manner. One of the concerns of the implant delivery systems currently on the market is premature release at an undesired site in the patient's body during delivery of the implant. If an implant is released before it arrives at the intended location, not only is the intended purpose not achieved, the implant may also pose a danger to the patient at the undesired location until the implant is repositioned or removed.

Another problem with many of the known delivery systems is that they can often adversely affect proper positioning of the device that is being implanted, which forces the doctor to estimate and take into consideration such effect when assessing the final implant position prior to releasing the implant. For example, most of the delivery systems include an elongated catheter that is used to access various passageways inside a patient's body. Often the desired position of the implant may not align with the longitudinal axis of the catheter. If the juncture between the implant and the catheter lacks sufficient flexibility, tension will be generated at the juncture when the implant has to be bent off the catheter's axis in order to assume the desire position. Upon release of the implant, the tension will affect both the implant and the delivery catheter, causing shifting in the implant position, and possible trauma to the surrounding tissue as the distal end of the catheter springs back to a more relaxed state. Such shifting in the implant position may result in a less desirable medical result (such as a residual leak in the case of septal occluders). Further, because of the possibility of trauma to surrounding tissues and organs, later device embolization may occur.

Implants may include devices designed for compression into a small size tube or catheter to facilitate their introduction into the vasculature of the patient. The implants are subsequently expandable either to occlude defects or holes in the heart, in the case of septal occluders, or to contact the walls of the passageway (e.g., blood vessels), in the case of vena cava filters or stents. Among these devices are septal occluders well-known in the art such as the occluder described in U.S. Pat. No. 5,425,744 issued to Fagan et al. Septal occluders are useful in treating medical conditions such as patent foramen ovale (PFO), which is a persistent, one-way, often flap-like opening in the wall between the right atrium and left atrium of the heart, as well as other congenital and acquired defects in the heart or vasculature.

Presently, ball-to-ball (or pin-to-pin) attach/release mechanisms, such as the attach/release mechanism illustrated in *Transcatheter Therapy in Pediatric Cardiology* (1993): 335-348, have been employed by one skilled in the art to implant and position such septal occluders within the heart. The pin-to-pin mechanism illustrates the adverse effect the attachment juncture may cause in the positioning of the implant. With pin-to-pin mechanisms, the implant, a septal occluder, for example, is held nearly perpendicular to the longitudinal axis of a sleeve on the distal end of the delivery catheter. Due to the acute angle of delivery of the septal occluder from the inferior vena cava to the septal wall, the rigid pin-to-pin connection applies tension to the implant and the underlying septum, and compromises precise assessment of the final implant position upon release of the implant.

Other types of attachment mechanisms known in the art include threaded male and female members as described in U.S. Pat. No. 5,725,552 issued to Kotula et al. This system, however, requires axial rotation of the members with respect to each other to disconnect the delivery device and also provides little flexibility, if any, for the lateral pivoting of the implant at the point it is attached to the delivery device.

Accordingly, there is a need for an interventional delivery system that prevents premature release of the attached implant, provides precise positioning of the implant, and also allows recapture of the implant.

SUMMARY OF THE INVENTION

The present invention provides novel and improved attachment systems and related methods, useful for delivering, repositioning, and removal of an implant, such as a septal occluder, into and out of a patient.

The invention relates to an interventional transcatheter delivery system that utilizes magnetic forces as part of an attachment system. In one aspect of the invention, the attachment surface on the attachment device is curved, which allows the reversibly attached target surface on the implant to pivot. In another aspect of the invention, the attachment device can be either the distal section of a core wire or the distal section of a tubular sleeve section in the delivery catheter.

According to one aspect of the invention, an interventional transcatheter delivery system capable of delivering or relocating an implant in a patient is provided. The system includes an elongated tubular portion, a core wire that slides inside the lumen of the tubular portion, an attachment device positioned at the distal end of the core wire and an implant having a target surface that is magnetically attachable to an attachment surface of the attachment device. The target surface and the attachment surface interface to permit the implant to pivot relative to the longitudinal axis of the core wire. Either the target surface, the attachment surface, or both may be magnetic.

In an embodiment of the invention, the attachment device is electromagnetic. In another embodiment, the attachment device includes a permanent magnet, such as a rare earth magnet. In yet another embodiment, between the attachment surface of the attachment device and the target surface of the implant, one is substantially concave, and the other is substantially convex, e.g., substantially spherical. In one embodiment, the target surface of the implant and the attachment surface of the attachment device interlock within the lumen of the tubular portion of the transcatheter delivery system. In one embodiment, the transcatheter delivery system further includes a releasing element such as a pushrod or a tubular component that releases the implant from the attachment device.

In an embodiment of the invention, the degree of pivoting for the implant relative to the axis of the core wire, while remaining attached, is no less than 90 degrees. In another embodiment, the implant is a septal occluder.

According to another aspect of the invention, an interventional transcatheter delivery system capable of delivering or relocating an implant in a patient is provided. The system includes an elongated tubular portion with a distal sleeve section. The distal sleeve section has an attachment surface.

The system further includes an implant having a target surface that is magnetically attachable to the attachment surface. Either or both of the surfaces can be magnetic.

In an embodiment of the invention, the distal sleeve section is electromagnetic. In another embodiment, the distal sleeve section includes a permanent magnet, such as a rare earth magnet. In yet another embodiment, the target surface of the implant is substantially convex, e.g., substantially spherical. In one embodiment, the attachment surface of the distal sleeve section is smooth and curved. The system may further include a releasing element such as a pushrod or a tubular sleeve that releases the implant from the distal sleeve section.

According to another aspect of the invention, a method for delivering an implant into a patient is provided. Steps of the method include providing an interventional transcatheter delivery system that has an elongated tubular portion and an attachment device positioned at the distal end of the tubular portion. The attachment device has an attachment surface. An implant is magnetically attached to the attachment surface of the attachment device through a target surface on the implant. After the transcatheter delivery system is advanced in a patient to a desired location, the implant is released and the transcatheter delivery system is withdrawn from the patient.

According to another aspect of the invention, a method for relocating an implant previously inside a patient is also provided. Steps of the method includes providing an interventional transcatheter delivery system that has an elongated tubular portion and an attachment device positioned at the distal end of the tubular portion. The attachment device has a curved attachment surface. The transcatheter delivery system is advanced in a patient until the distal end of the system's tubular portion is in the vicinity of an implant already inside the patient. After implant is magnetically attached to the attachment surface of the attachment device through a target surface on the implant, the transcatheter delivery system is relocated, thereby relocating the implant. Then the implant is released from the attachment device.

BRIEF DESCRIPTION OF THE DRAWINGS

In the drawings, like reference numbers generally refer to the same parts throughout the different views. Also, the drawings are not necessarily to scale, emphasis instead generally being placed upon illustrating the principles of the invention.

DETAILED DESCRIPTION OF THE PRESENT INVENTION

In accordance with the present invention, attachment devices utilizing one or more magnets as part of an interventional transcatheter delivery system for attaching a medical implant to the transcatheter delivery system are provided. For example, the implant may be magnetically attached to an attachment device at the distal end of a core wire slidingly moveable within the transcatheter delivery system, or the implant may be magnetically attached to an attachment device in the distal sleeve section of the catheter. In one aspect, the system of the invention provides a mechanism for pivoting the implant with respect to the transcatheter delivery system in order to avoid bending the catheter during the delivery and positioning of the implant in a patient. In another aspect, the attachment device of the invention reduces the likelihood of premature release of the implant. In yet another aspect, the transcatheter delivery system can be used to reattach, i.e., capture, an implant in a patient's body for repositioning in or for extracting the implant from the patient's body. Moreover, aspects of the invention can be used in combination with other attachment or coupling mechanisms, including all kinds of grippers, forceps, retainers and couplers, to achieve an intended function more efficiently and safely.

The term "implant" used herein includes devices, carriers, and objects that are placed in the body of a patient by invasive or minimally invasive methods, including but not limited to, prosthetic occluders, stents, filters, prostheses, valves, pumps, pace-makers, medications and so on. The implant may be permanent, semi-permanent, or temporary. The implant may be biodegradable. The implant may be removable through an interventional procedure. The implant may be a drug delivery device, such as capsules, tablets, or suppositories, for example, those that deliver pharmaceutical agents to the patient. In particular, the term implant includes intracardiac prosthetic occluders, for example, septal occluders for the treatment of, for example, patent foramen ovale.

The terms "magnet" and "magnetic" used herein refer to a material that is capable of asserting an attractive or repulsive force on another material. Magnets and magnetic materials include but are not limited to, permanent magnets such as rare earth magnets (e.g., samarium-cobalt and neodymium-iron-boron), ceramic magnets, and Alnico magnets, magnetizable materials (e.g., ferromagnetic materials), electromagnets, and so on. The term "ferromagnetic material" as used herein refers to a material that has relatively high magnetic permeability and can be permanently magnetized upon application of an external magnetic field. Ferromagnetic materials typically contain, for example, iron, nickel, cobalt, stainless steel, or compounds thereof. The term "paramagnetic material" as used herein refers to a material that is attracted toward magnets, but does not become permanently magnetized.

Figure 1A:
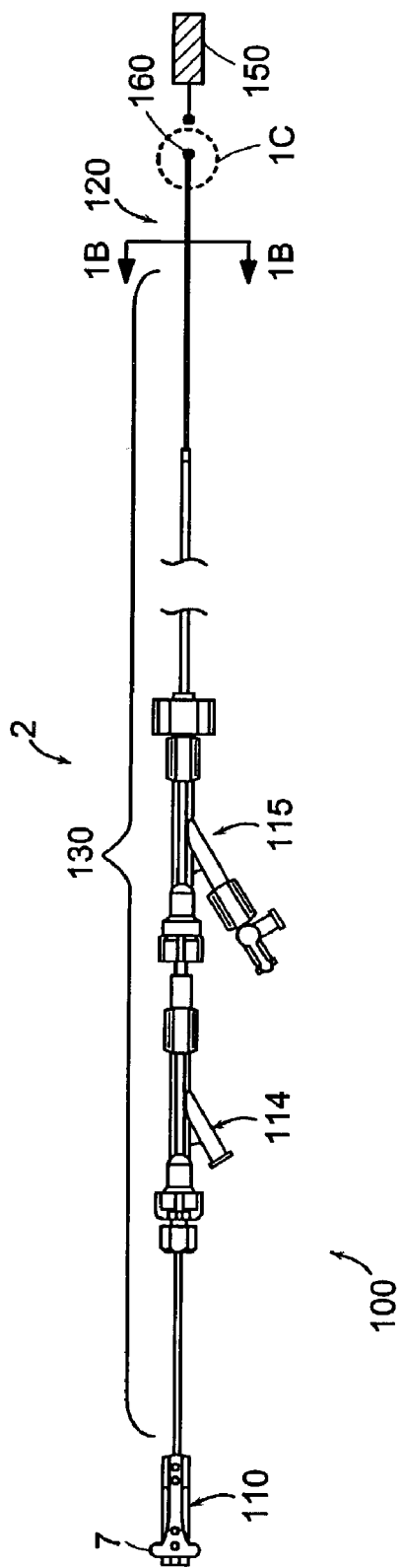
FIG. 1A illustrates a plan view of an embodiment of a transcatheter delivery system.

Referring to FIG. 1A, in one embodiment according to the invention, an interventional transcatheter delivery system 2 includes a catheter 100 having a proximal handle 110, a distal section 120, and an elongated body portion 130 extending between and connecting the handle 110 to the distal section 120. The body portion 130 may include various elongated coaxial tubes. The distal section 120 includes one or more lumens (FIG. 1B) which parallel the longitudinal axis of the distal section 120. The distal section 120 terminates with an attachment device 160 (details shown in FIG. 1C). The transcatheter delivery system 2 may further include an implant 150.

Figure 1C:
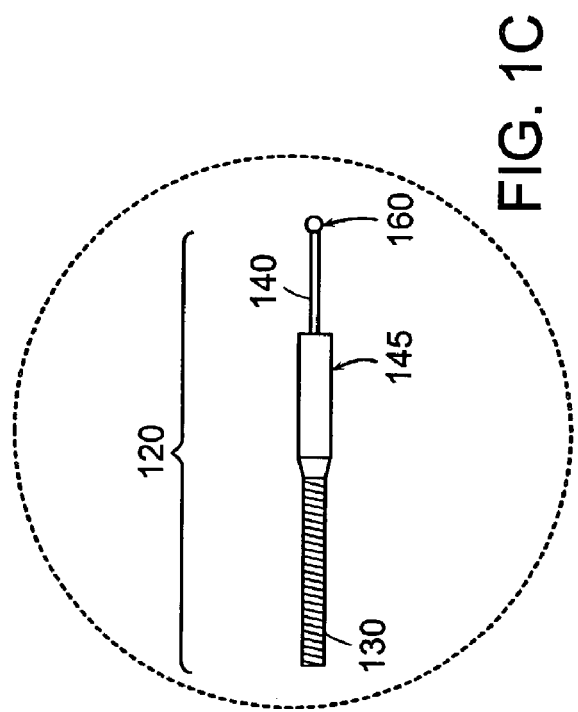
FIG. 1C illustrates the detail of the distal section designated under the circle "C" in FIG. 1A, of one embodiment of the catheter illustrated in FIG. 1A.
Figure 1B:
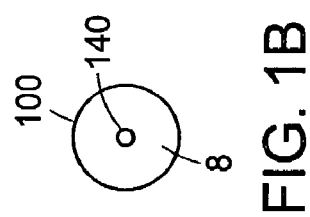
FIG. 1B illustrates a cross-section, taken in the plane indicated by the line 1B-1B in FIG. 1A, of one embodiment of the distal end of the catheter illustrated in FIG. 1A.

Referring to FIG. 1B, a cross-section traversing the longitudinal axis of the catheter 100 is shown. There is at least one lumen 8 axially disposed in the catheter 100. The lumen 8 may span the length of the catheter 100. A core wire 140 is axially and slideably disposed in the lumen 8 of the catheter 100.

Referring now to FIG. 1C, in one embodiment, the distal section 120 of the catheter 100 includes the core wire 140 having a longitudinal axis and extending from the handle 110 (FIG. 1A) through the lumen 8 (FIG. 1B) of the catheter 100 to the distal section 120. The distal end of the distal section 120 may further include a tubular sleeve 145. The sleeve 145 is connected to the elongated body portion 130 of the catheter 100. The sleeve 145 and the elongated body portion 130 of the catheter 100 can have the same outer diameter. Axial and sliding movement of the core wire 140 in the lumen 8 of the catheter 100 relative to the sleeve 145 can be effected by an actuator 7 (FIG. 1A) operatively joined to the core wire 140 located in the handle 110 (FIG. 1A). In an alternative embodiment, the catheter 100 is operatively joined to the actuator 7 and the core wire 140 remains stationary or fixed while the sleeve 145 or catheter 100 is actuated by the actuator 7 to move the sleeve 145 axially over the core wire 140. The handle 110 may also include a locking mechanism (not shown) that locks in the relative positions between the core wire 140 and the catheter 100 or the sleeve 145. For example, the core wire 140 may be extended from the distal end of sleeve 145 or, alternatively, the core wire 140 may be retracted (not shown) into the lumen 8 (FIG. 1B) of sleeve 145 by actuation of the actuator 7 in the handle 110 and such positions can be maintained by the locking mechanism on the handle 110. The distal section 120 of the catheter 100 further includes an attachment device 160 in accordance with the present invention described below.

Figure 2A:
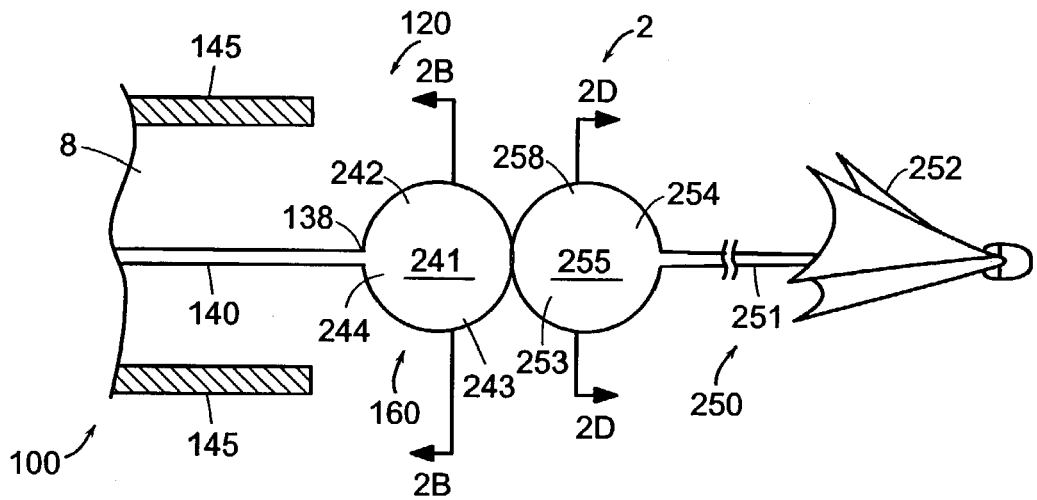
FIG. 2A illustrates a partially cut-off view of the distal end of a transcatheter delivery system including an attachment device and an implant in a first pivotal position in accordance with an embodiment of the invention.
Figure 2B:
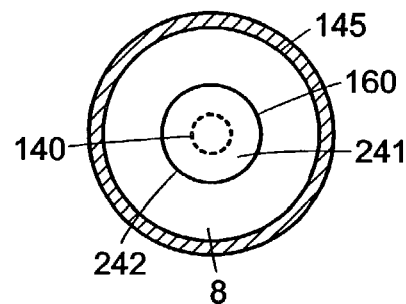
FIG. 2B illustrates a cross-section, taken in the plane indicated by the line 2B-2B in FIG. 2A, of one embodiment of the distal end of the transcatheter delivery system illustrated in FIG. 2A.

Referring to FIGS. 2A and 2B, in an embodiment of the present invention, the distal end 120 of the catheter 100 includes the sleeve 145 and the attachment device 160. The attachment device 160, for example, may be connected to the distal end 138 of the core wire 140, e.g., by an extruding process, molding, soldering, welding, or an adhesive. The attachment device 160 is axially moveable in the lumen 8 of the distal end 120 of the catheter 100 through actuating the core wire 140 by the actuator 7 in the handle 110 (FIG. 1A).

Figure 2C:
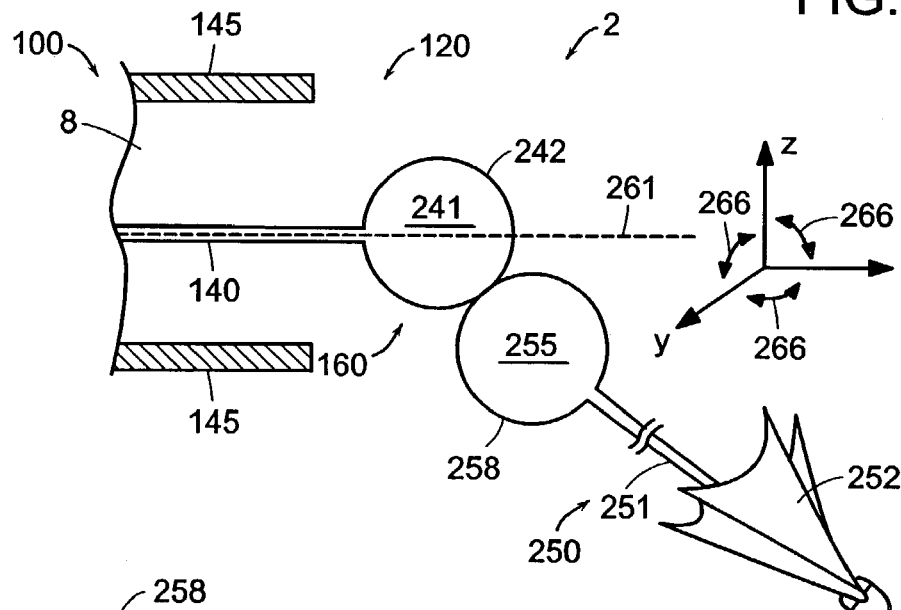
FIG. 2C illustrates the transcatheter delivery system in FIG. 2A with the implant in a second pivotal position.

Still referring to FIGS. 2A and 2B, in one embodiment, according to the invention, the attachment device 160 is an enlargement of distal tip 241 of the core wire 140 (hereinafter referred to as the "wire tip 241"), i.e., the distal tip 241 of the core wire 140 has a greater maximum cross-sectional area than the maximum cross-sectional area of the rest of the core wire 140, thereby providing the attachment device 160 of the transcatheter delivery system 2. The attachment device 160 may include a curved attachment surface. In one embodiment according to the invention, the attachment device 160, i.e., the wire tip 241, shown in FIGS. 2A-2C, is substantially spherical and provides a substantially convex attachment surface 242. Other shapes of the attachment device 160 are also contemplated by the invention and the invention is not limited by the shapes illustrated.

With continued reference to FIG. 2A, in one embodiment, according to the invention, the attachment device 160 is magnetic. For example, the wire tip 241 may be wholly or partially made of a permanent magnet, such as a rare earth magnet, providing a convex, magnetic, attachment surface 242. Attachment device 160, namely, the wire tip 241, includes two magnetic poles 243 and 244, corresponding to either of the North or South polarity, respectively. In another embodiment, the attachment device 160, namely, the wire tip 241, is ferromagnetic.

Referring still to FIG. 2A, in one embodiment according to the invention, an implant 250 may be, for example, a septal occluder. In this embodiment, the septal occluder 250 has a wire 251 extending from a main body 252 of the septal occluder 250. The tip 255 of the wire 251 of the implant 250 is reversibly attachable to the attachment device 160 of the transcatheter delivery system 2 through magnetic attraction. In one embodiment, the implant tip 255 is ferromagnetic or paramagnetic and is made of, for example, steel, and is magnetically attachable to the magnetic wire tip 241 of the core wire 140 of the transcatheter delivery system 2. In another embodiment, the implant tip 255 is magnetic and is magnetically attachable to the ferromagnetic or paramagnetic wire tip 241. In yet another embodiment, both the implant tip 255 and the wire tip 241 are magnetic. The implant tip 255 may include, for example, two magnetic poles 253 and 254, each corresponding to one of the South and North polarities. Pole 243 in the wire tip 241 and the pole 253 in the implant tip 255 are of opposite polarities and therefore effect attachment through magnetic attraction.

Still referring to FIG. 2A, because magnetic forces can be strong, for example, with rare earth magnets, using a magnet as part of the attachment mechanism can help prevent premature release of the implant 250 during implant delivery in the body of a patient. Moreover, if the operator decides to adjust the implant position or remove the implant 250 after releasing it in the patient's body, the wire tip 241 of the attachment device 160 and the implant tip 255 of the implant 250 can be reattached through magnetic attraction, offering another operational advantage absent in conventional transcatheter delivery devices.

In each embodiment of the transcatheter delivery system 2 of the present invention, either the attachment device of the delivery catheter 100 or its target, i.e., a part of the implant such as the implant tip, is magnetic. The other can be ferromagnetic or paramagnetic and therefore, attracted to the magnetic structure. For ease of understanding, the attachment device of the delivery catheter 100 is often arbitrarily termed "magnetic" in the specification and its target in the implant is often termed "ferromagnetic or paramagnetic." But it should be noted that designations of magnetic and ferromagnetic/paramagnetic could be applied to either the attachment device or the implant with no bearing on the principle of the invention. Further, both the attachment device and its target in the implant can be magnetic.

Figure 2D:
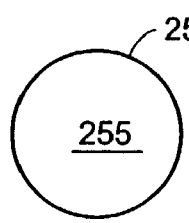
FIG. 2D illustrates a cross-section, taken in the plane indicated by the line 2D-2D in FIG. 2A, of one embodiment of the implant tip illustrated in FIG. 2A.

Referring to FIGS. 2A and 2D, the ferromagnetic or paramagnetic implant tip 255 may have a variety of shapes. In a particular embodiment, the implant tip 255 includes a substantially convex surface, or, alternatively, a concave surface. In one embodiment according to the invention, the implant tip 255 includes a substantially convex target surface 258, e.g., a surface on a sphere as a counterpart surface to the magnetic convex surface 242 provided by the attachment device 160 at the wire tip 241.

Referring to FIGS. 2B and 2C, because in one embodiment of the transcatheter delivery system 2 according to the invention, the wire tip 241 also has a substantially convex attachment surface 242, any point on the target surface 258 of the implant tip 255 can be magnetically coupled to any point on the attachment surface 242 of the wire tip 241. Therefore, in a three dimensional reference system illustrated in FIG. 2C by axes x, y, and z, where the x-axis parallels the longitudinal axis 261 of the core wire 140, the implant tip 255 pivots, in any plane or direction. In other words, the implant tip 255 may pivot, as indicated by arrow 266, in the x-y, y-z, z-x planes or any combination of any number of the three planes without losing the magnetic attachment between the target surface 258 of the implant tip 255 and the attachment surface 242 of the attachment device 160. The pivot by the implant tip 255, indicated by the arrow 266, in any given plane is between 0 and 360°, for example, 45°, 90°, or 180°, as dictated by the geometry of the surfaces 242 and 258. In a particular embodiment where both the wire tip 241 and the implant tip 255 are substantially spherical, depending on the thickness of the core wire 140, the degree of pivot, indicated by the arrow 266, in any given plane, can approach 360°. Also, the implant 250 can freely rotate, as indicated by arrow 270, around its own longitudinal axis, without losing magnetic attachment to the attachment device 160.

The advantage in pivotability according to the invention is the ability to precisely position the implant 250 by the operator. When the implant 250 is able to pivot relative to the axis 261 of the core wire 140, it is less likely to cause tension in the implant 250 or in the delivery catheter 100 when the implant 250 assumes its implant position. As a result, upon release of the implant 250, the likelihood of shifting in the implant or the catheter position that may cause trauma to surrounding tissues is lessened.

Figure 3A:
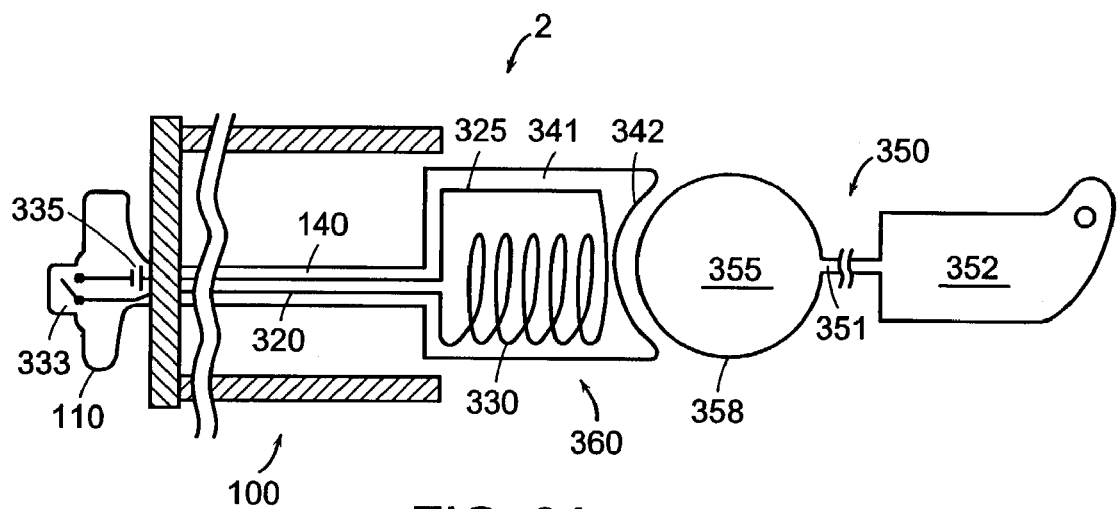
FIG. 3A illustrates a cross-sectional view of a transcatheter delivery system including an attachment device and an implant in a first pivotal position in accordance with another embodiment of the invention.
Figure 3B:
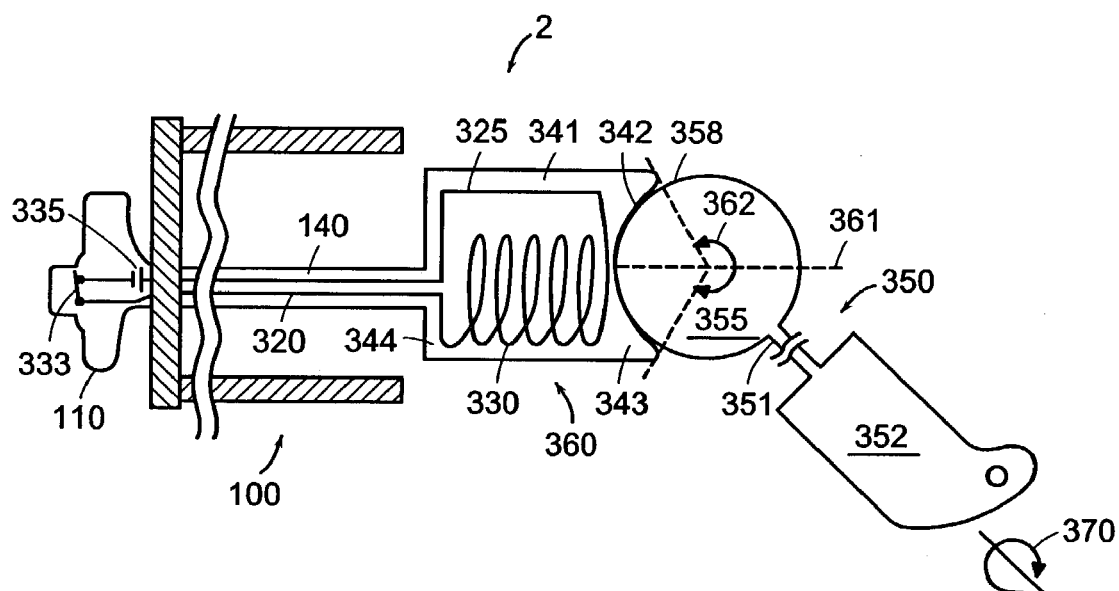
FIG. 3B illustrates the transcatheter delivery system of FIG. 3A with the implant in a second pivotal position.

Referring now to FIGS. 3A and 3B, an alternative embodiment of the present invention includes a transcatheter delivery system 2 with a catheter 100 having a distal attachment device 360. The attachment device 360 includes a wire tip 341 connected through an elongated member, e.g., the core wire 140, to the proximal handle 110 of the catheter 100. An electric wire 320 is operatively connected, e.g., at its distal portion 325, to the attachment device 360 and, e.g., at its proximal end, to a power source 335. The power source in one embodiment is a battery 335 disposed in the handle 110 or to some other external power source (not shown). The electric wire 320 may extend within the core wire 140 as long as the core wire 140 is insulated to protect the operator and patient from receiving an unintended electrical discharge. In one embodiment, the distal portion 325 of the electric wire 320 is shaped into a coil 330 disposed within the wire tip 341. The coil 330 can be disposed elsewhere, e.g., close to the proximal handle 110, in the transcatheter delivery system 2, as long as the magnetic field generated by the coil 330 is effectively transmitted, e.g., through ferromagnetic components of the core wire 140 to the distal section of the wire tip 341. A power switch 333 is also optionally disposed in the handle 110 and connected in series with the power source (e.g., the battery 335), both of which are electrically connected across the terminal of the electrical coil 330.

In the particular embodiment of the interventional transcatheter delivery system 2 shown in FIGS. 3A and 3B, the distal, attachment surface 342 of the wire tip 341 is substantially concave, although other shapes are contemplated by the present invention such as a substantially convex shape. The interventional delivery system 2 also includes an implant 3.50 which has a body 352, and an attachment tip 355 secured to the main body 352 through a tether 351. The attachment tip 355 has a substantially convex, e.g., spherical, target surface 358. The implant body 352 may be, for example, a prosthetic occluder or, as illustrated in FIGS. 3A and 3B, a urinary prosthesis. The substantially convex, target surface 358 of the attachment tip 355 is ferromagnetic or paramagnetic and couples with the substantially concave, attachment surface 342 of the attachment device 360 to form a "ball-and-socket" configuration.

Referring now to FIG. 3B, when the power switch 333 in the delivery catheter handle 110 is closed, an electric current flows through the coil 330 generating a magnetic field with two poles 343 and 344. The force generated by the magnetic field is proportional to the magnitude of the current and the number of turns in the coil 330. Once the magnetic field is generated, the target surface 358 on the ferromagnetic or paramagnetic attachment tip 355 of the implant 350 reversibly attaches to the attachment surface 342 of the attachment device 360 through magnetic attraction. This "ball-and-socket" configuration is relatively shallow permits a looser fit between the attachment surface 342 and the target surface 358. In the "ball-and-socket" embodiment of the present invention, a tight fit between the implant 350 and the attachment device 360 is not necessary because the magnetic attraction holds the attachment device 360 and the implant 350 together.

As shown in FIG. 3B, the attachment surface 342 extending from the delivery catheter 100 and the target surface 358 of the implant 350 are coupled together. The attachment tip 355 can freely rotate about its own axis without losing the magnetic coupling with the attachment surface 342. The attachment tip 355 can also pivot relative to the longitudinal axis 361 of the core wire 140 while remaining magnetically attached to the attachment surface 342. The degree of pivoting 362 for the implant 350 relative to the longitudinal axis 361 of the core wire 140 depends on the configuration of the wire tip 341 and can be between 0 to 360°, for example, 180° or 270°. In the particular embodiment illustrated in FIGS. 3A and 3B, also depending on the thickness of the implant tether 351, the degree of pivoting 362 for the implant 350 approach 270°. Also, the "ball-and-socket" configuration functions substantially the same if the concave ("socket") surface is on the implant 350, and the convex ("ball") surface is on the attachment device 360. Additionally, the implant 350 can freely rotate, as indicated by arrow 370, around its own longitudinal axis without losing magnetic attachment to the attachment device 360.

Figure 4A:
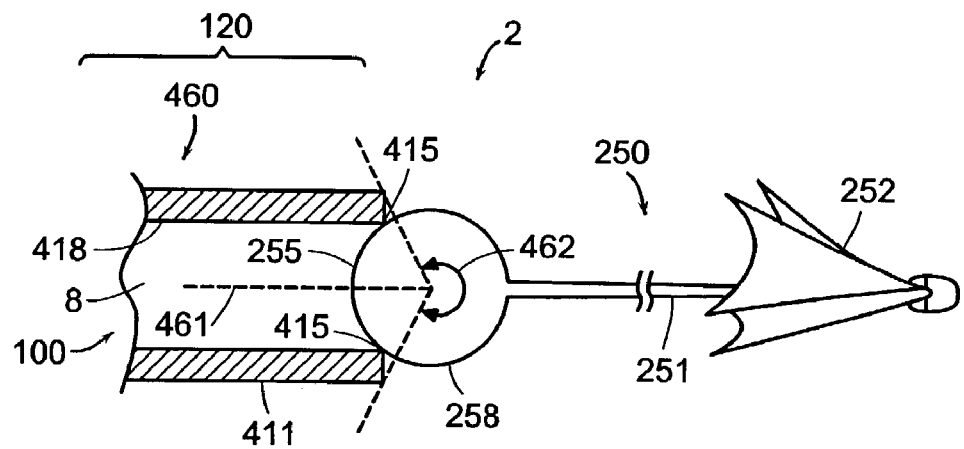
FIG. 4A illustrates another embodiment of the transcatheter delivery system in accordance with the invention.

Referring now to FIG. 4A, in another embodiment of the transcatheter delivery system 2 of the present invention, the delivery catheter 100 has an attachment device 460 consisting of a tubular sleeve section 411 disposed at the distal end of the catheter 100. The tubular sleeve section 411 of the catheter 100 has an inner distal rim 415 at the inner surface 418 of the lumen 8 of the distal section 120 of the catheter 100. At least the inner distal rim 415 of the tubular sleeve section 411 is magnetic. The interventional delivery system 2 may further include an implant 250 which may have a substantially convex, e.g., spherical, implant tip 255 that is connected to the main body 252 of the implant 250 through a wire 251 and described above in connection with FIGS. 2A, 2C and 2D. The implant tip 255 has a substantially convex, e.g., spherical, ferromagnetic, target surface 258, which reversibly attaches to the inner distal rim 415 of the catheter 100 through magnetic attraction such that a portion of the target surface 258 is positioned in the lumen 8 of the tubular sleeve section 411 and the target surface 258 contacts the inner surface 418 of the lumen 8 of the tubular sleeve section 411, for example, the inner rim 415 of the tubular sleeve section 411. The substantially convex, implant tip 255 may also rotate freely about its own axis without losing the magnetic coupling with the distal inner rim 415 of the catheter 100.

The substantially convex surface 258 can also pivot relative to the longitudinal axis 461 of the tubular sleeve section 411 while remaining magnetically attached to the distal inner rim 415 of the tubular sleeve section 411. The implant 250 may pivot relative to the longitudinal axis 461 of the distal sleeve section 411, illustrated by angle 462 in FIG. 4A, in the range between 0 and 360°, for example, 180° or 270°, while retaining magnetic attachment to the attachment device 460. In the particular embodiment where the implant tip 255 is substantially convex, depending on the relative dimension between the implant tip 255 and the inner distal rim 415, and depending on the thickness of the implant wire 251, the degree of pivot by the implant 250, illustrated by the angle 462 in FIG. 4A, can approach 360°. For example, if the inner distal rim 415 has a relatively small diameter, compared to the diameter of a spherical implant tip 255, such that the portion of the target surface 258 in the lumen 8 of the tubular sleeve section 411 is a very small portion of the target surface 258, the angle 462 can be close to 360°.

Figure 4B:
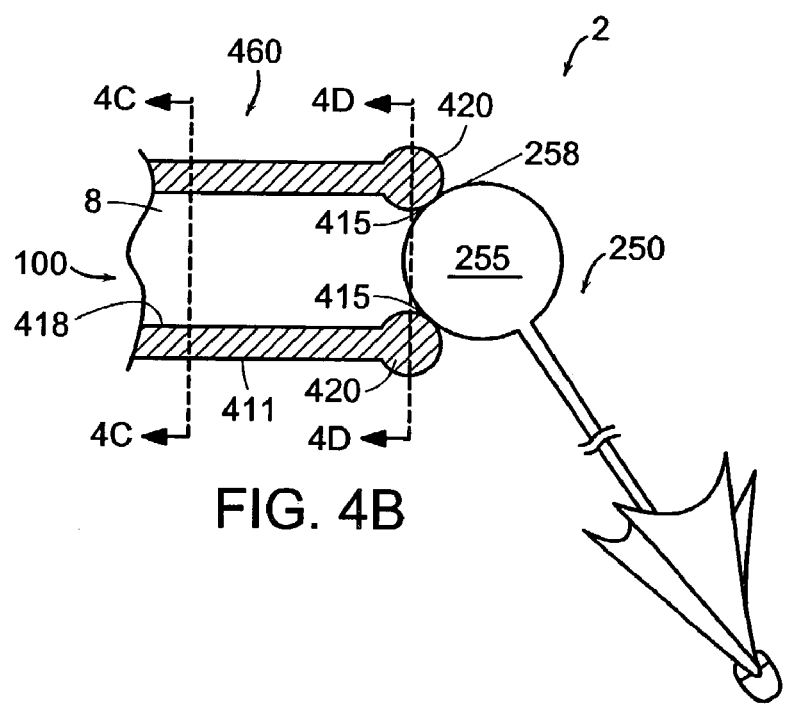
FIG. 4B shows an alternative embodiment of the transcatheter delivery system in accordance with the invention.
Figure 4C:
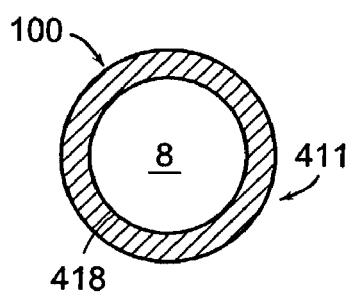
FIGS. 4C and 4D illustrate cross-sectional views of the transcatheter delivery system of FIG. 4B, taken in planes indicated by the lines 4C-4C and 4D-4D, respectively.
Figure 4D:
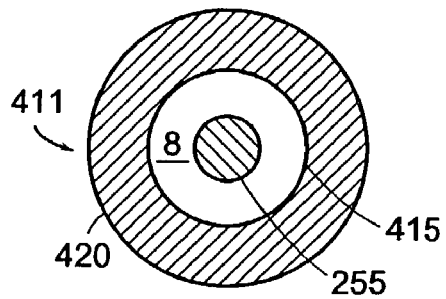

Referring now to FIG. 4B, in another embodiment of the transcatheter delivery system 2 according to the invention, the attachment device 460 includes a tubular sleeve section 411 with an inner surface 418 defining a lumen 8. The tubular sleeve section 411 further includes a distal end 420. Referring to FIGS. 4B and 4D, the distal end 420 is a circumferentially expanded part of the distal sleeve section 411 near or at the inner distal rim 415 compared to the portion proximal to the distal end 420 illustrated in FIG. 4C. The lumen 8 of the distal sleeve section 411 is narrowed at the inner distal rim 415, by the expanded distal end 420. In a particular embodiment, according to the invention, the expanded distal end 420 of the distal sleeve section 411 is rounded, providing a smooth and curved, attachment surface for magnetic coupling by the attachment surface 258 of the implant 250. A smooth and curved attachment surface may be advantageous in facilitating coupling between the attachment device 460 and the implant tip 255. The distal end 420 is magnetic and the ferromagnetic/paramagnetic implant tip 255 reversibly attaches to the distal end 420 through magnetic coupling. The implant tip 255 can rotate and pivot as described in connection with the embodiment of the transcatheter delivery system illustrated in FIG. 4A.

Figure 5A:
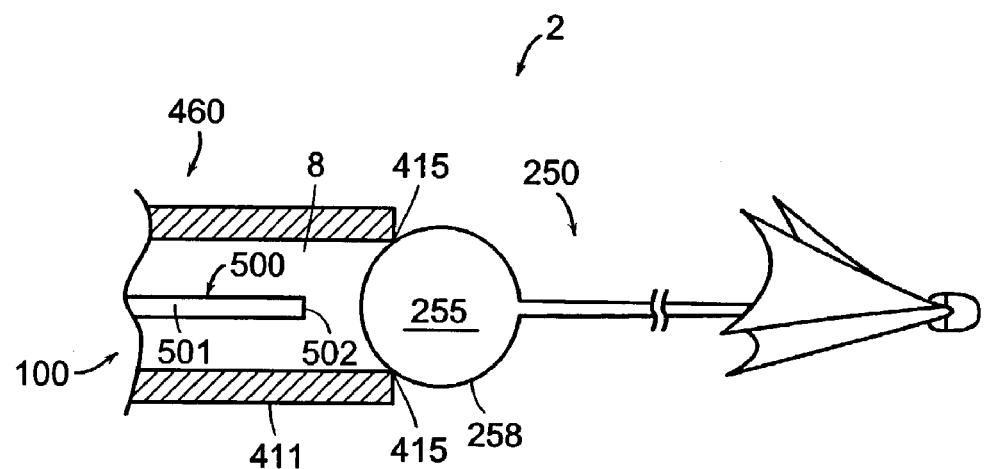
FIGS. 5A and 5B illustrate one embodiment of the releasing element of the transcatheter delivery system in accordance with the invention.
Figure 5B:
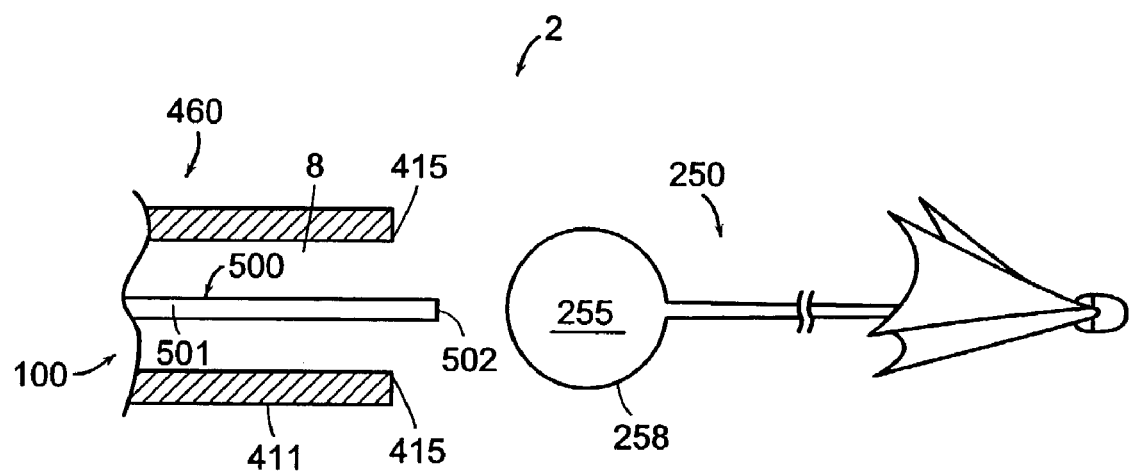

Referring now to FIGS. 5A and 5B, in another embodiment according to the invention, the interventional transcatheter delivery system 2 includes a releasing element 500. The releasing element 500, e.g., a pushrod 501 is slidingly moveable in the lumen 8 of the distal sleeve section 411 of the catheter 100, to aid in mechanically pushing the implant 250 distally away from the attachment device 460 by advancing the releasing element 500 in the distal direction. The releasing element 500 is operatively connected to the proximal handle (FIG. 1) of the delivery catheter 100 through an actuation mechanism (not shown). The distal surface 502 of the releasing element 500 contacts the target surface 258 on the implant tip 255 during its advance. Further advance of the releasing element 500 causes the target surface 258 to separate from the attachment surface, for example, to separate from the inner edge 415 of the sleeve section 411. As a result, the implant 250 is released from the attachment device 460. The releasing element 500 may be made of, for example, metal. In one embodiment, the releasing element 500 is made of a material that is not attracted to a magnet, e.g., plastic. In one embodiment, the distal surface 502 of the releasing element 500 is flat.

Still referring to FIGS. 5A and 5B, the releasing element 500 exerts a force sufficient to counter the magnetic attraction between the attachment device 460 and the implant 250, causing their separation (FIG. 5B). Preferably, a locking mechanism (not shown) is operatively associated with the releasing element 500 to prevent premature release of the implant 250.

Figure 5C:
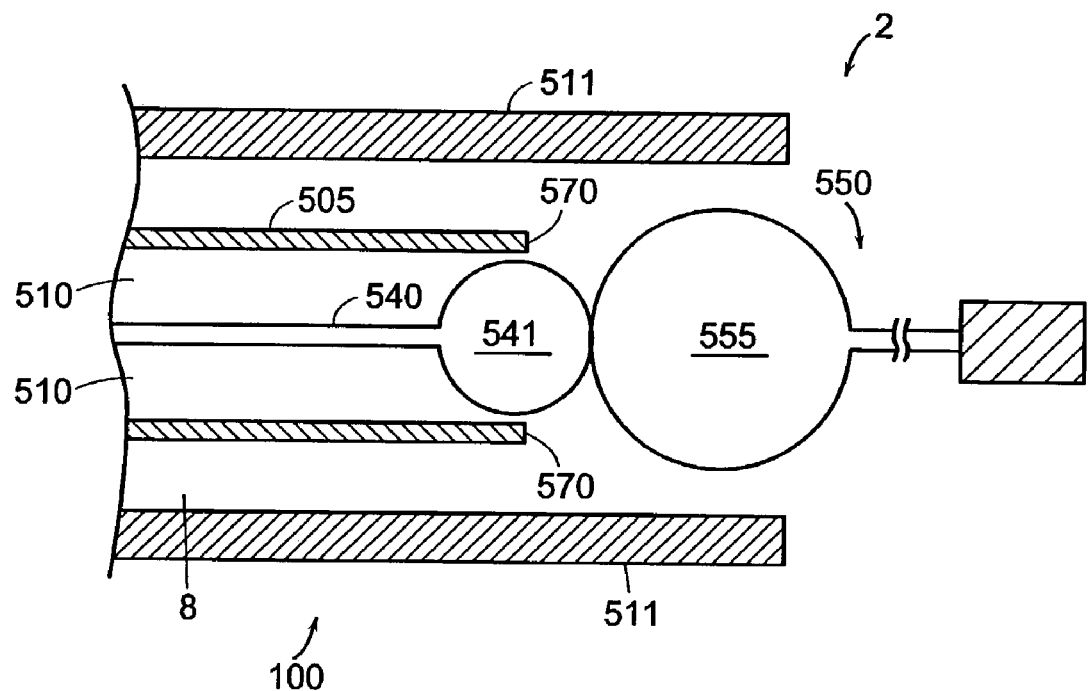
FIGS. 5C and 5D illustrate another embodiment of the releasing element of the transcatheter delivery system in accordance with the invention.

Referring now to FIG. 5C, in one embodiment, the interventional transcatheter delivery system 2 includes a tubular elongated member 505 having a lumen 510 and a distal end 570. The tubular elongated member 505 is coaxial with and slidingly moveably in the lumen 8 of the distal sleeve section 511 in the catheter 100 of the interventional transcatheter delivery system 2. A core wire 540 and a magnetic wire tip 541 positioned at the distal end of the core wire 540 are slidingly moveable in the lumen 510 of the tubular elongated member 505. In one embodiment according to the invention, the tubular elongated member 505 may be used as a releasing element 500 to separate a ferromagnetic or paramagnetic implant tip 555 of an implant 550 from the magnetic wire tip 541.

Figure 5D:
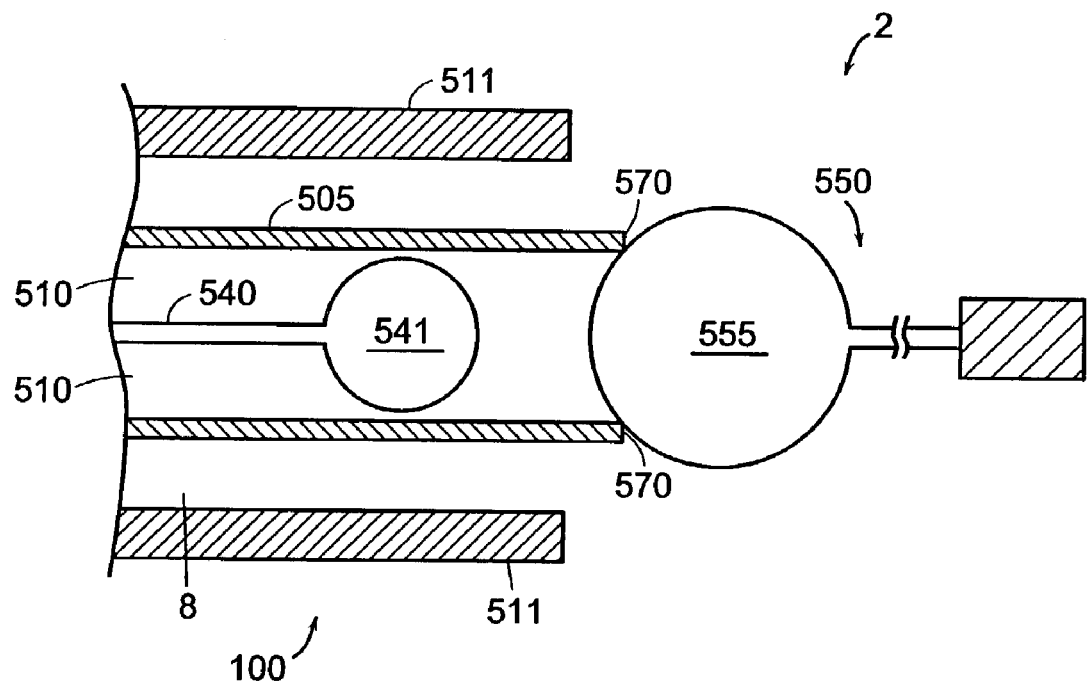

For example, referring now to FIG. 5D, in one embodiment according to the invention, the inner diameter of the tubular elongated member 505 is at least as large as the maximal cross-sectional dimension, e.g., the diameter, of the wire tip 541, such that the tubular elongated member 505 can slide over the wire tip 541 when the tubular elongated member 505 is advanced distally in the lumen 8 of the distal sleeve section 511 or when the wire tip 541 is withdrawn proximally into the lumen 510 of the tubular elongated member 505. The diameter of the ferromagnetic/paramagnetic implant tip 555 is larger than the inner diameter of the tubular elongated member 505. By advancing the elongated tubular member 505 distally, or by withdrawing the core wire 540 proximally, the distal end 570 of the tubular elongated member 505 contacts the implant tip 555. The elongated tubular member 505 may exert a force on the implant tip 555 sufficient to counter the magnetic attraction between the wire tip 541 and the implant tip 555, causing their separation.

The tubular elongated member 505 may be made of, for example, a non-ferromagnetic material such as plastic.

In another embodiment of the electromagnetic attachment device 360 illustrated in FIGS. 3A and 3B, and described in the corresponding text above, the releasing element may be an electrical switching mechanism 333 that closes the electrical circuit to the electromagnetic attachment device 360. For example, referring again to FIGS. 3A and 3B, a switch, such as a toggle switch that controls the mechanism 333, can be such a releasing element. When the switch 333 is opened, the electromagnetic field is extinguished, causing the ferromagnetic/paramagnetic implant 350 to separate from the electromagnetic attachment device 360.

Figure 6A:
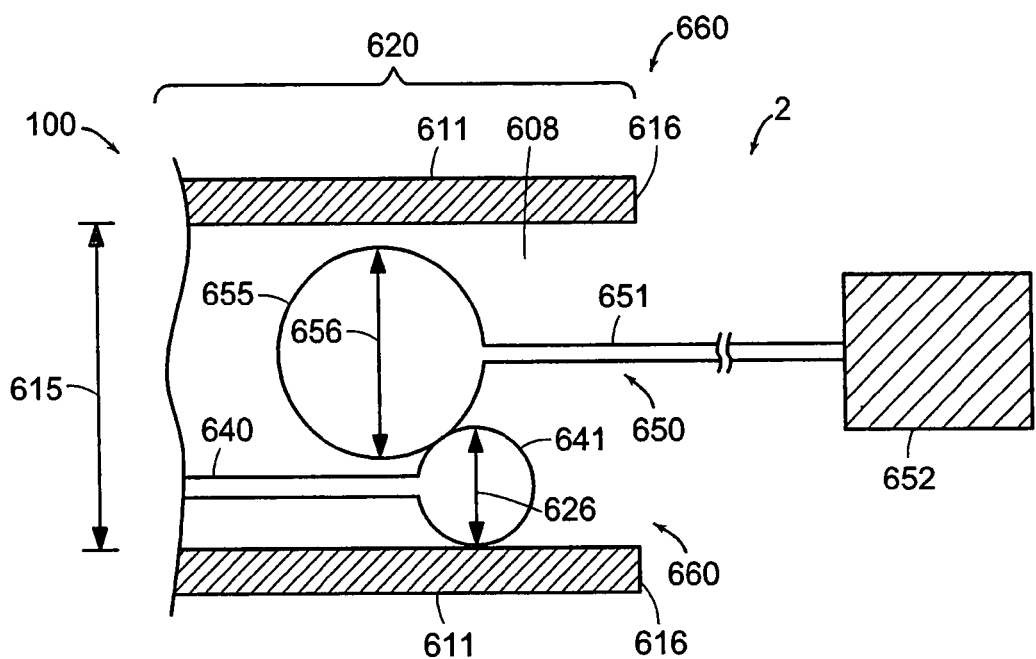
FIG. 6A illustrates a transcatheter delivery system having an interlocking "ball-toball" configuration in accordance with an embodiment of the invention.
Figure 6B:
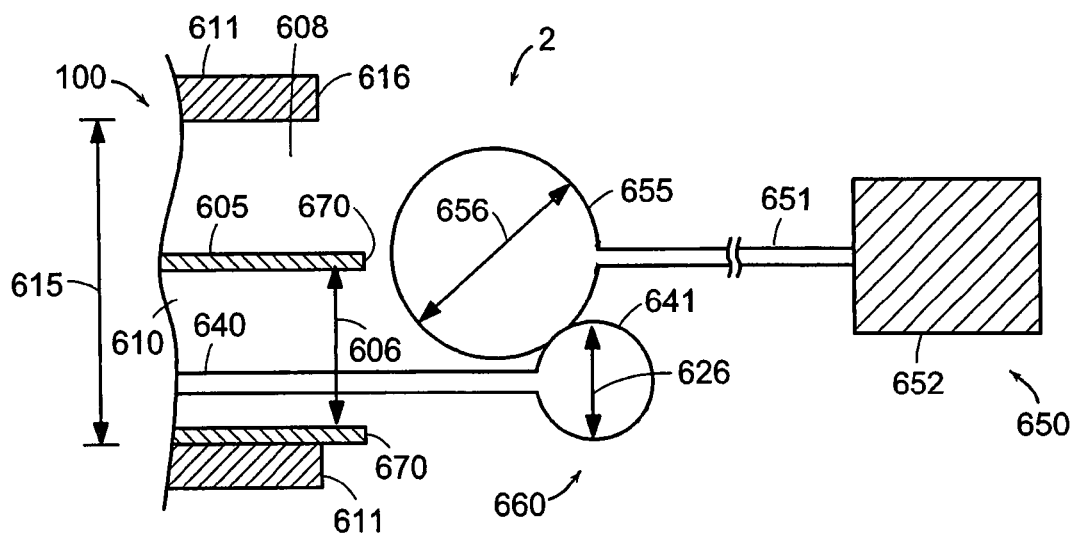
FIGS. 6B and 6C illustrate another embodiment of a transcatheter delivery system having an interlocking "ball-to-ball" configuration and a releasing element in accordance with the invention.
Figure 6C:
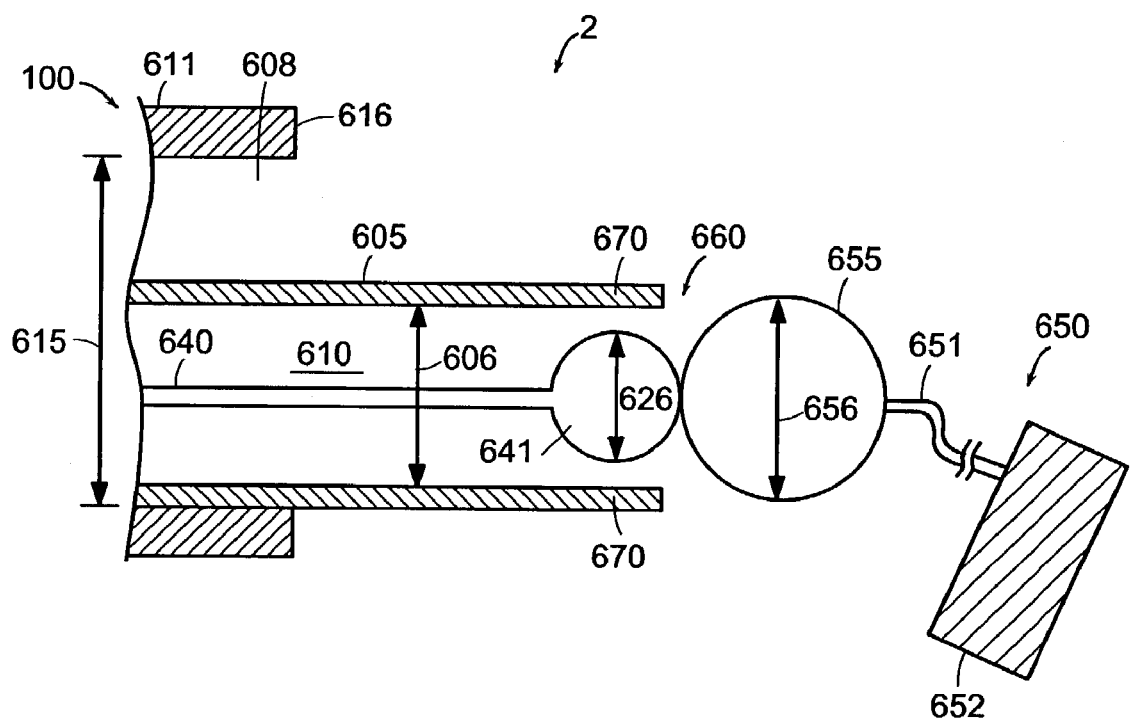

Referring now to FIGS. 6A-6C in another embodiment of the transcatheter delivery system 2, an attachment device 660 is disposed at the distal end 620 of the delivery catheter 100 and includes a distal sleeve section 611 having a lumen 608. The lumen 608 has a diameter 615. A core wire 640 is slidingly moveable in the lumen 608 of the distal sleeve section 611, and is operatively connected to a proximal handle 110 (FIG. 1) of the delivery catheter 100. The core wire 640 has an enlarged wire tip 641 positioned at the distal end, e.g., the wire tip 641 is substantially spherical with a diameter 626. An implant 650 has an attachable implant tip 655 secured to a main body 652 through a wire 651. In one embodiment, the implant tip 655 may be substantially spherical with a diameter 656. The inner diameter 615 of the sleeve 611 is less than the combined diameters of the wire tip 641 and the implant tip 655. For example, the inner diameter 615 of the distal sleeve section 611 may be 0.040 inches, the diameter 626 of the wire tip 641 may be about 0.026 inches, and the diameter 656 of the implant tip 655 may be about 0.018 inches. Accordingly, when the core wire tip 641 is closer to the distal end 616 of the sleeve 611 than the implant tip 655, the wire tip 641 blocks the implant tip 655 from exiting the sleeve 611. Such an interlocking configuration keeps at least part of the implant 650 locked inside the distal sleeve section 611 of the delivery catheter 100. Additionally, the core wire tip 641 may be magnetic and the implant tip 655 may be ferromagnetic, or vise versa. Accordingly, the core wire tip 641 and the implant tip 655 are reversibly interlocked by additional magnetic means, providing additional security against premature release of the implant 650.

Referring now to FIG. 6B, when the core wire tip 641 and the implant tip 655 are extended from the distal sleeve section 611, without magnetic attraction, the two would separate. However, due to the magnetic attraction, the implant tip 655 stays attached to the wire tip 641. In this configuration, illustrated in FIG. 6B, the implant 650 may pivot relative to the longitudinal axis of the core wire 640.

Referring now to FIG. 6C, the implant tip 655 may also move across the surface of the wire tip 641 without losing magnetic attachment. The ability of the implant tip 655 to pivot relative to the core wire 640 and to move across the surface of the wire tip 641 is especially advantageous when the operator of the delivery catheter needs to ascertain the precise position of the implant 650 after extending the implant 650 from the distal sleeve section 611. Because the implant tip 655 remains attached to the wire tip 641, the operator can adjust the position of the implant 650 or even reposition it without losing magnetic attachment between the implant tip 655 and the wire tip 641.

Again referring to FIG. 6B, in one embodiment, the interventional transcatheter delivery system 2 includes a tubular elongated member 605, with an inner diameter 606, that slides inside the lumen 608 of the distal sleeve section 611. The inner diameter 606 of the tubular elongated member 605 is the same or slightly larger than the maximal cross-sectional dimension, e.g., the diameter 626, of the wire tip 641, such that the tubular elongated member 605 can slide over the wire tip 641 of the core wire 640 when the tubular elongated member 605 is advanced distally in the lumen 608 of the distal sleeve section 611 or when the wire tip 641 is withdrawn proximally into the lumen 610 of the tubular elongated member 605. When the tubular component 605's distal end 670 contacts the implant tip 655, it can force the implant tip 655 off the wire tip 641, completing the release.

Referring again to FIG. 6C, the diameter 656 of the implant tip 655 is larger than the inner diameter 606 of the tubular elongated member 605, which is, in turn, larger than the diameter 626 of the wire tip 641. The differences in diameters ensures that the tubular elongated member 605 can slide over the wire tip 641 but not the implant tip 656. Therefore, even when the wire tip 641 and the implant tip 655 are attached to each other in a position shown in FIG. 6C, the releasing element, i.e., the tubular elongated member 605, can effectively separate the two tips (641, 655). Specifically, by advancing the tubular elongated member 605, or by withdrawing the core wire 640, the distal end 670 of the tubular elongated member 605 contacts the implant tip 655. The tubular elongated member 605 may exert a force sufficient to counter the magnetic attraction between the wire tip 641 and the implant tip 655, causing their separation. The tubular elongated member 605 may be made of a non-ferromagnetic material such as plastic, for example.

In the embodiment where the core wire tip 641 is electromagnetic, the releasing element for the attachment device 660, as described above, can be an electromagnetic switching mechanism that opens and closes the electrical circuit that supplies the magnetic field.

In another aspect, the invention provides methods for using the magnetic transcatheter delivery system 2 described above. For example, the implant is first attached securely to the distal tip of the delivery catheter of the present invention through, at least partly, magnetic attraction. Referring again to FIG. 2A, in an exemplary procedure for treating PFO, an implant 250, in this case, a septal occluder, is collapsed into the lumen 8 of the distal sleeve 145 of the delivery catheter 100 after a ferromagnetic or paramagnetic spherical implant tip 255 in the proximal end of the occluder 250 is magnetically attached to the magnetic spherical wire tip 241 of the core wire 140. After the occluder 250 is collapsed into the lumen 8 of the sleeve 145, the position of the core wire 140 relative to the sleeve 145 is locked through a locking mechanism (not shown) inside the proximal handle 110 (FIG. 1A).

The femoral vein in a patient, for example, is selected for vascular access and delivery of the occluder by the transcatheter delivery system 2 to the heart. For example, a 10 Fr, 75 cm long, hemostasis control introducer sheath may be used for occluder delivery.

Referring again to FIG. 2B, after the occluder 250 is delivered to the implant site, for example, a defect in the atrial septum, the operator unlocks the core wire 140 from its position inside the sleeve 145 by an actuator (not shown) on the handle 110 (FIG. 1A) and advances the core wire 140 distally until the wire tip 241 is extended from the sleeve 145. The operator may rotate and pivot the implant tip 255 on the wire tip 241 while the wire tip 241 and the implant tip 255 are still magnetically attached to each other, thereby adjusting the position of the occluder 250. After confirming the location of the occluder 250, the operator releases the occluder 250, optionally using a releasing element described above. After releasing the occluder 250, as long as the wire tip 241 is still outside the distal sleeve 145, reattachment of the implant tip 255 for repositioning or retrieving the occluder 250 is possible.

The transcatheter delivery system in accordance with the present invention can also be used for the sole purpose of relocating an implant that is already positioned in a patient's body. Any of the above-described embodiments can be used for relocating the implant. The transcatheter delivery system is inserted into a patient's body until the magnetic tip of the attachment device is near or adjacent the attachment structure (e.g., a ferromagnetic/paramagnetic tip) of an implant, and the attachment device and the implant attach to each other through magnetic attraction. After attachment of the implant is confirmed, relocating, i.e., repositioning or retrieval of the implant becomes possible. After relocation is completed, the implant may be released from the attachment device.

Other Embodiments

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An interventional transvascular delivery system for delivering or relocating an implant in the cardiovascular system of a patient, the system comprising:
   an elongated tubular portion defining a lumen and having an internal diameter;
   a releasing element slideably moveable in the lumen of said elongated tubular portion comprising a tubular elongated member comprising a distal end, and a lumen having an internal diameter for releasing said implant from the delivery system;
   a core wire slidably moveable in the lumen of the tubular elongated member comprising a distal end;
   an attachment device positioned at the distal end of the core wire and comprising an attachment surface and a diameter; and
   an implant including a tip having a target surface, said tip positioned at the proximal end of the implant and having a diameter larger than the internal diameter of the lumen of the tubular elongate member;
   wherein the attachment surface reversibly binds to the target surface of said implant for delivering and relocating said implant in said patient, wherein both the attachment surface of the attachment device and the target surface of the implant are substantially spherical, and the combined diameter of the attachment device and the implant tip is greater than the internal diameter of the elongated tubular portion.

2. The system of claim 1 wherein the attachment surface of the attachment device is magnetic.

3. The system of claim 2 wherein the attachment device is electromagnetic.

4. The system of claim 2 wherein the attachment device comprises a permanent magnet.

5. The system of claim 4 wherein the permanent magnet comprises a rare earth magnet.

6. The system of claim 1 wherein the target surface of the implant is magnetic.

7. The system of claim 6 wherein the implant comprises a permanent magnet.

8. The system of claim 1 wherein the attachment surface comprises a diameter sufficient for interlocking with the target surface within the lumen of the tubular portion.

9. The system of claim 1 wherein the attachment surface comprises a first substantially spherical surface of a first diameter, the target surface of said implant comprises a second substantially spherical surface of a second diameter, and the tubular elongated member has a diameter that is no smaller than the first diameter and no larger than the second diameter.

10. The system of claim 1 wherein the implant comprises a septal occluder.

11. The system of claim 1 wherein the implant pivots relative to the longitudinal axis of the core wire for no less than 90 degrees.

12. The system of claim 1 wherein the releasing element comprises an electromagnetic switching mechanism.

13. The system of claim 1 wherein the proximal end of the implant tip is proximal to the attachment device when the attachment device is bound to the target surface of the implant.

14. The system of claim 13 wherein the attachment device and the implant tip are positioned in the lumen of the elongated tubular portion and the attachment device blocks the implant tip from exiting the elongated tubular portion.

15. An interventional transvascular delivery system for delivering or relocating an implant in the cardiovascular system of a patient, the system comprising:
   an elongated tubular portion defining a lumen and having an internal diameter;
   a releasing element slideably moveable in the lumen of said elongated tubular portion comprising a tubular elongated member comprising a distal end, and a lumen having an internal diameter for releasing said implant from the delivery system;
   a core wire slidably moveable in the lumen of the tubular elongated member comprising a distal end;
   an attachment device positioned at the distal end of the core wire and comprising an attachment surface and a diameter; and
   an implant including a tip having a target surface, said tip positioned at the proximal end of the implant and having a diameter larger than the internal diameter of the lumen of the tubular elongate member;
   wherein the attachment surface reversibly binds to the target surface of said implant for delivering and relocating said implant in said patient, wherein one of the attachment surface of the attachment device and the target surface of the implant is substantially concave and the other is substantially convex, and the combined diameter of the attachment device and the implant tip is greater than the internal diameter of the elongated tubular portion.

16. The system of claim 15 wherein the substantially convex surface is substantially spherical.

* * * * *